US009658149B2

(12) United States Patent
Freese et al.

(10) Patent No.: US 9,658,149 B2
(45) Date of Patent: May 23, 2017

(54) DEVICES HAVING ONE OR MORE INTEGRATED COMPUTATIONAL ELEMENTS AND METHODS FOR DETERMINING A CHARACTERISTIC OF A SAMPLE BY COMPUTATIONALLY COMBINING SIGNALS PRODUCED THEREWITH

(75) Inventors: Robert Freese, Pittsboro, NC (US); Christopher Michael Jones, Houston, TX (US); David Perkins, The Woodlands, TX (US); Michael Simcock, Columbia, SC (US); William Soltmann, The Woodlands, TX (US)

(73) Assignee: HALLIBURTON ENERGY SERVICES, INC., Houston, TX (US)

(*) Notice: Subject to any disclaimer, the term of this patent is extended or adjusted under 35 U.S.C. 154(b) by 827 days.

(21) Appl. No.: 13/456,255

(22) Filed: Apr. 26, 2012

(65) Prior Publication Data
US 2013/0284894 A1    Oct. 31, 2013

(51) Int. Cl.
| | | |
|---|---|---|
| *G01N 21/17* | (2006.01) | |
| *G01N 21/31* | (2006.01) | |
| *G06E 3/00* | (2006.01) | |

(52) U.S. Cl.
CPC .......... *G01N 21/17* (2013.01); *G01N 21/314* (2013.01); *G06E 3/001* (2013.01); *G01N 2021/3177* (2013.01); *G01N 2021/3196* (2013.01)

(58) Field of Classification Search
CPC ................................................ H01L 27/14621
(Continued)

(56) References Cited

U.S. PATENT DOCUMENTS

| | | |
|---|---|---|
| 3,488,491 A | 1/1970 | Schuman |
| 4,761,073 A | 8/1988 | Meltz et al. |
| | (Continued) | |

FOREIGN PATENT DOCUMENTS

| | | |
|---|---|---|
| EP | 1061355 A1 | 12/2000 |
| EP | 1969326 | 9/2008 |
| | (Continued) | |

OTHER PUBLICATIONS

Official Action for Australian Patent Application No. 2013 252841 dated Nov. 10, 2014.
(Continued)

*Primary Examiner* — Tony Ko
(74) *Attorney, Agent, or Firm* — McDermott Will & Emery LLP (57) ABSTRACT

Optical computing devices containing one or more integrated computational elements may be used to produce two or more detector output signals that are computationally combinable to determine a characteristic of a sample. The devices may comprise a first integrated computational element and a second integrated computational element, each integrated computational element having an optical function associated therewith, and the optical function of the second integrated computational element being at least partially offset in wavelength space relative to that of the first integrated computational element; an optional electromagnetic radiation source; at least one detector configured to receive electromagnetic radiation that has optically interacted with each integrated computational element and produce a first signal and a second signal associated therewith; and a signal processing unit operable for computationally combining the first signal and the second signal to determine a characteristic of a sample.

16 Claims, 5 Drawing Sheets

(58) Field of Classification Search
USPC .................. 250/208.1, 214 R, 216, 214.1
See application file for complete search history.

(56) References Cited

U.S. PATENT DOCUMENTS

| | | | |
|---|---|---|---|
| 4,795,262 A | 1/1989 | Morris et al. | |
| 4,806,012 A | 2/1989 | Meltz et al. | |
| 4,882,492 A | 11/1989 | Schlager | |
| 5,399,854 A | 3/1995 | Dunphy et al. | |
| 5,426,506 A | 6/1995 | Ellingson et al. | |
| 5,493,390 A | 2/1996 | Varasi et al. | |
| 5,737,076 A * | 4/1998 | Glaus .................. | G01J 3/28 356/310 |
| 6,091,504 A | 7/2000 | Walker et al. | |
| 6,198,531 B1 | 3/2001 | Myrick et al. | |
| 6,268,911 B1 | 7/2001 | Tubel et al. | |
| 6,529,276 B1 | 3/2003 | Myrick | |
| 6,576,188 B1 | 6/2003 | Rose et al. | |
| 7,123,844 B2 | 10/2006 | Myrick | |
| 7,138,156 B1 | 11/2006 | Myrick et al. | |
| 7,332,094 B2 | 2/2008 | Abney et al. | |
| 7,472,748 B2 | 1/2009 | Gdanski et al. | |
| 7,623,233 B2 | 11/2009 | Freese et al. | |
| 7,671,973 B2 | 3/2010 | Van Beek et al. | |
| 7,697,141 B2 | 4/2010 | Jones et al. | |
| 7,712,527 B2 | 5/2010 | Roddy | |
| 7,834,999 B2 | 11/2010 | Myrick et al. | |
| 7,911,605 B2 | 3/2011 | Myrick et al. | |
| 7,920,258 B2 | 4/2011 | Myrick et al. | |
| 7,934,556 B2 | 5/2011 | Clark et al. | |
| 8,049,881 B2 | 11/2011 | Myrick et al. | |
| 8,141,633 B2 | 3/2012 | Hampton et al. | |
| 8,253,619 B2 | 8/2012 | Holbrook et al. | |
| 8,345,234 B2 | 1/2013 | Myrick et al. | |
| 8,345,243 B2 | 1/2013 | Ghinovker et al. | |
| 8,547,556 B2 | 10/2013 | Irani | |
| 8,780,352 B2 | 7/2014 | Freese et al. | |
| 8,823,939 B2 | 9/2014 | Freese et al. | |
| 8,879,053 B2 | 11/2014 | Freese et al. | |
| 8,902,423 B2 * | 12/2014 | Myrick ............ | G01J 3/4406 356/319 |
| 8,908,165 B2 | 12/2014 | Tunheim et al. | |
| 8,912,477 B2 * | 12/2014 | Freese et al. .......... | 250/208.2 |
| 8,941,046 B2 | 1/2015 | Freese et al. | |
| 8,960,294 B2 | 2/2015 | Freese et al. | |
| 8,997,860 B2 | 4/2015 | Freese et al. | |
| 9,013,698 B2 | 4/2015 | Freese et al. | |
| 9,013,702 B2 | 4/2015 | Freese et al. | |
| 2001/0020675 A1 | 9/2001 | Tubel et al. | |
| 2002/0023752 A1 | 2/2002 | Qu et al. | |
| 2002/0071121 A1 | 6/2002 | Ortyn et al. | |
| 2002/0109080 A1 | 8/2002 | Tubel et al. | |
| 2003/0056581 A1 | 3/2003 | Turner et al. | |
| 2003/0145988 A1 | 8/2003 | Mullins et al. | |
| 2004/0045705 A1 | 3/2004 | Gardner et al. | |
| 2004/0129884 A1 | 7/2004 | Boyle et al. | |
| 2006/0102343 A1 | 5/2006 | Skinner et al. | |
| 2006/0142955 A1 | 6/2006 | Jones et al. | |
| 2006/0158734 A1 | 7/2006 | Schuurmans et al. | |
| 2006/0183183 A1 | 8/2006 | Felkner et al. | |
| 2007/0177240 A1 | 8/2007 | Van Beek et al. | |
| 2007/0248488 A1 | 10/2007 | Denkewicz | |
| 2007/0282647 A1 | 12/2007 | Freese et al. | |
| 2007/0291251 A1 | 12/2007 | Rensen et al. | |
| 2008/0041594 A1 | 2/2008 | Boles et al. | |
| 2008/0094623 A1 | 4/2008 | Schuurmans et al. | |
| 2008/0133193 A1 | 6/2008 | Gdanski et al. | |
| 2008/0231849 A1 | 9/2008 | Myrick et al. | |
| 2008/0276687 A1 | 11/2008 | Myrick et al. | |
| 2008/0309930 A1 | 12/2008 | Rensen | |
| 2009/0002697 A1 | 1/2009 | Freese et al. | |
| 2009/0015819 A1 * | 1/2009 | Van Beek et al. .......... | 356/39 |
| 2009/0033933 A1 | 2/2009 | Myrick et al. | |
| 2009/0073433 A1 | 3/2009 | Myrick et al. | |
| 2009/0087912 A1 | 4/2009 | Ramos et al. | |
| 2009/0097024 A1 | 4/2009 | Blackburn et al. | |
| 2009/0137887 A1 | 5/2009 | Shariati et al. | |
| 2009/0140144 A1 | 6/2009 | Myrick et al. | |
| 2009/0154288 A1 | 6/2009 | Heathman | |
| 2009/0182693 A1 | 7/2009 | Fulton et al. | |
| 2009/0205821 A1 | 8/2009 | Smith | |
| 2009/0213380 A1 | 8/2009 | Appel et al. | |
| 2009/0216504 A1 | 8/2009 | Priore et al. | |
| 2009/0219512 A1 | 9/2009 | Myrick et al. | |
| 2009/0219538 A1 | 9/2009 | Myrick et al. | |
| 2009/0219539 A1 | 9/2009 | Myrick et al. | |
| 2009/0245718 A1 | 10/2009 | Li et al. | |
| 2009/0250613 A1 | 10/2009 | Myrick et al. | |
| 2009/0299946 A1 | 12/2009 | Myrick et al. | |
| 2009/0305330 A1 | 12/2009 | Kroon et al. | |
| 2009/0316150 A1 | 12/2009 | Myrick et al. | |
| 2010/0006292 A1 | 1/2010 | Boles et al. | |
| 2010/0027014 A1 | 2/2010 | Hart et al. | |
| 2010/0042348 A1 * | 2/2010 | Bakker ........................ | 702/85 |
| 2010/0050905 A1 | 3/2010 | Lewis et al. | |
| 2010/0051266 A1 | 3/2010 | Roddy et al. | |
| 2010/0051275 A1 | 3/2010 | Lewis et al. | |
| 2010/0073666 A1 | 3/2010 | Perkins et al. | |
| 2010/0084132 A1 | 4/2010 | Noya et al. | |
| 2010/0141952 A1 | 6/2010 | Myrick et al. | |
| 2010/0148785 A1 | 6/2010 | Schaefer et al. | |
| 2010/0149523 A1 | 6/2010 | Heideman et al. | |
| 2010/0149537 A1 | 6/2010 | Myrick et al. | |
| 2010/0153048 A1 | 6/2010 | Myrick et al. | |
| 2010/0182600 A1 | 7/2010 | Freese et al. | |
| 2010/0195105 A1 | 8/2010 | Myrick et al. | |
| 2010/0245096 A1 | 9/2010 | Jones et al. | |
| 2010/0265509 A1 | 10/2010 | Jones et al. | |
| 2010/0302539 A1 | 12/2010 | Myrick et al. | |
| 2010/0305741 A1 | 12/2010 | Myrick | |
| 2010/0326659 A1 | 12/2010 | Schultz et al. | |
| 2010/0328669 A1 | 12/2010 | Myrick et al. | |
| 2011/0048708 A1 | 3/2011 | Glasbergen et al. | |
| 2011/0063086 A1 | 3/2011 | Oishi | |
| 2011/0163046 A1 | 7/2011 | Neal et al. | |
| 2011/0197662 A1 | 8/2011 | McAlister | |
| 2011/0199610 A1 | 8/2011 | Myrick et al. | |
| 2012/0187283 A1 | 7/2012 | Yamada et al. | |
| 2012/0211650 A1 | 8/2012 | Jones et al. | |
| 2012/0250017 A1 | 10/2012 | Morys et al. | |
| 2013/0031964 A1 * | 2/2013 | Tunheim et al. ............ | 73/61.48 |
| 2013/0031970 A1 | 2/2013 | Freese et al. | |
| 2013/0031971 A1 | 2/2013 | Freese et al. | |
| 2013/0031972 A1 | 2/2013 | Freese et al. | |
| 2013/0032333 A1 | 2/2013 | Freese et al. | |
| 2013/0032340 A1 | 2/2013 | Freese et al. | |
| 2013/0033701 A1 * | 2/2013 | Tunheim et al. ............ | 356/73 |
| 2013/0033702 A1 | 2/2013 | Tunheim et al. | |
| 2013/0034842 A1 | 2/2013 | Tunheim et al. | |
| 2013/0284895 A1 * | 10/2013 | Freese et al. .......... | 250/208.2 |
| 2013/0284896 A1 | 10/2013 | Freese et al. | |
| 2013/0284897 A1 | 10/2013 | Freese et al. | |
| 2013/0284898 A1 | 10/2013 | Freese et al. | |
| 2013/0284899 A1 | 10/2013 | Freese et al. | |
| 2013/0284900 A1 | 10/2013 | Freese et al. | |
| 2013/0284901 A1 | 10/2013 | Freese et al. | |
| 2013/0284904 A1 | 10/2013 | Freese et al. | |
| 2013/0286398 A1 | 10/2013 | Freese et al. | |
| 2013/0286399 A1 | 10/2013 | Freese et al. | |
| 2013/0287061 A1 | 10/2013 | Freese et al. | |
| 2014/0263974 A1 * | 9/2014 | Freese et al. .......... | 250/208.2 |
| 2014/0306096 A1 * | 10/2014 | Freese et al. .......... | 250/208.2 |

FOREIGN PATENT DOCUMENTS

| | | |
|---|---|---|
| EP | 2087328 | 8/2009 |
| EP | 2140238 | 1/2010 |
| EP | 2169384 A1 | 3/2010 |
| EP | 2320027 A1 | 5/2011 |
| GB | 2353310 A | 2/2001 |
| WO | 2004018840 A1 | 3/2004 |
| WO | 2004057285 A1 | 7/2004 |
| WO | 2005064314 A1 | 7/2005 |
| WO | 2006021928 A1 | 3/2006 |

(56) References Cited

FOREIGN PATENT DOCUMENTS

| WO | 2006110041 A1 | 10/2006 |
|---|---|---|
| WO | 2006114773 A1 | 11/2006 |
| WO | 2006137902 | 12/2006 |
| WO | 2007064575 | 6/2007 |
| WO | 2007098392 A2 | 8/2007 |
| WO | 2008057912 A2 | 5/2008 |
| WO | 2008057913 A2 | 5/2008 |
| WO | 2011063086 A1 | 5/2011 |
| WO | 2013162744 A1 | 10/2013 |
| WO | 2013162795 A1 | 10/2013 |
| WO | 2013162799 A1 | 10/2013 |
| WO | 2013162809 A1 | 10/2013 |
| WO | 2013162860 A1 | 10/2013 |
| WO | 2013162861 A1 | 10/2013 |
| WO | 2013162901 A1 | 10/2013 |
| WO | 2013162906 A1 | 10/2013 |
| WO | 2013162913 A1 | 10/2013 |
| WO | 2013162914 A1 | 10/2013 |

OTHER PUBLICATIONS

Official Action for Australian Patent Application No. 2013 252881 dated Nov. 12, 2014.
Myrick, et al. "Spectral Tolerance Determination for Multivariate Optical Element Design," Fresenuis' Journal of Analytical Chemistry, 369:2001; pp. 351-355.
Gdanski et al., "A New Model for Matching Fracturing Fluid Flowback Composition," 2007 SPE Hydraulic Fracturing Technology Conference held in College Station, Texas, SPE 106040.
Gdanski et al., "Using Lines-of-Solutions to Understand Fracture Conductivity and Fracture Cleanup," SPE Production and Operations Symposium held in Oklahoma City, OK, 2011, SPE 142096.
Myrick et al., "Application of Multivariate Optical Computing to Simple Near-Infrared Point Measurements," Proceedings of SPIE, US, vol. 4574, 2002, pp. 208-215, XP002391230.
Nelson et al., "Multivariate Optical Computation for Predictive Spectroscopy," Analytical Chemistry, vol. 70, No. 1, 1998, pp. 73-82, XP055067630.
Bialkowski, "Species Discrimination and Quantitative Estimation Using Incoherent Linear Optical Signal Processing of Emission Signals," Analytical Chemistry, vol. 58, No. 12, 1986, pp. 2561-2563, XP055067237.
Medendorp, et al., "Applications of Interated Sensing and Processing in Spectroscopic Imaging and Sensing," Journal of Chemometrics, vol. 19, No. 10, 2006, pp. 533-542, XP055067235.
Bin Dai et al., "Molecular Factor Computing for Predictive Spectroscopy," Pharmaceutical Research, Kluwer Academic Publishers-Plenum Publishers, NL, vol. 24, No. 8, 2007, pp. 1441-1449, XP019507244.
International Search Report and Written Opinion for PCT/US2013/036177 dated Jun. 28, 2013.
International Search Report and Written Opinion for PCT/US2013/036107 dated Jun. 28, 2013.
International Search Report and Written Opinion for PCT/US2013/033975 dated Jun. 28, 2013.
International Search Report and Written Opinion for PCT/US2013/035572 dated Jun. 28, 2013.
International Search Report and Written Opinion for PCT/US2013035604 dated Jun. 28, 2013.
International Search Report and Written Opinion for PCT/US2013/031467 dated Jun. 28, 2013.
International Search Report and Writen Opinion for PCT/US2013/031960 dated Jun. 28, 2013.
International Search Report and Written Opinion for PCT/US2013/032970 dated Jun. 28, 2013.
International Search Report and Written Opinion for PCT/US2013/033256 dated Jun. 28, 2013.
International Search Report and Written Opinion for PCT/US2013/033502 dated Jun. 28, 2013.
Sullivan et al. "Implementation of a Numerical Needle Method for Thin-Film Design," Applied Optics, vol. 35, No. 28, pp. 5484-5492, 1996.
Dobrowolski et al., "Refinement of Optical Multilayer Systems with Different Optimization Procedures," Applied Optics, vol. 29, No. 19, pp. 2876-2893, 1990.
Qu et al, "Fluorescence Spectral Imaging for Characterization of Tissue Based on Multivariate Statistical Analysis," Journal of the Optical Society of America, vol. 19, No. 9, 2002 XP055046065.
International Search Report and Written Opinion for PCT/US2013/036287 dated Aug. 2, 2013.
International Search Report and Written Opinion for PCT/US2013/036294 dated Aug. 7, 2013.
Official Action for Canadian Patent Application No. 2,842,703 dated Jul. 25, 2014.
Halliburton Brochure for "Acid-on-the-Fly (AOF) Blending System," published 2009.
Official Action for Australian Patent Application No. 2013252855 dated Apr. 15, 2015.
Dai et al., Molecular Factor Computing for Predictive Spectroscopy, Pharmaceutical Research, vol. 24, No. 8, 2007, pp. 1441-1449.
Mendendorp J., et al., Application of Integrated Sensing and Processing in Spectroscopic Imaging and Sensing, Journal of Chemometrics, vol. 19, 2005, pp. 533-542.
Soyemi et al., Design and Testing of a Multivariate Optical Element: The First Demonstration of Multivariate Optical Computing for Predictive Spectroscopy, 73 Anal. Chem. 1069-1079 (Feb. 10, 2001).
Official Action for Australian Patent Application No. 2013252890 dated Jul. 11, 2015.

* cited by examiner

DEVICES HAVING ONE OR MORE INTEGRATED COMPUTATIONAL ELEMENTS AND METHODS FOR DETERMINING A CHARACTERISTIC OF A SAMPLE BY COMPUTATIONALLY COMBINING SIGNALS PRODUCED THEREWITH

BACKGROUND

The present disclosure relates to devices and methods for determining a characteristic of a sample using one or more integrated computational elements, and, more specifically, to devices and methods that computationally combine detector output signals produced from electromagnetic radiation that has optically interacted with one or more integrated computational elements.

Spectroscopic techniques for measuring various characteristics of materials are well known and routinely used under laboratory conditions. In cases where there is not extensive sample matrix interference, spectroscopic techniques can sometimes be carried out without using an involved sample preparation. It is more common, however, to carry out various sample preparation procedures before conducting the analysis. Reasons for conducting sample preparation procedures before carrying out an analysis can include, for example, removing interfering background materials from the sample, converting an analyte of interest into a chemical form that can be better detected by a chosen spectroscopic technique, concentrating a low concentration analyte, and/or adding standards to improve the accuracy of quantitative measurements. Sample preparation steps can result in delays of hours to days when obtaining an analysis. Furthermore, there can be additional delays associated with transporting the sample to a laboratory equipped to carry out the analysis.

Although spectroscopic techniques can, at least in principle, be conducted at a job site in real-time or near real-time, the transitioning of spectroscopic instruments from the laboratory into a field or process environment can be expensive and complex. For example, conditions such as inconsistent temperature, humidity, and vibration can be commonly encountered during field or process use, and they can be difficult to compensate for with conventional spectroscopic instruments. At a minimum, these conditions and others can affect the calibration and durability of many types of spectroscopic instruments. Further, field personnel may not have the training needed to satisfactorily carry out a spectroscopic analysis and take appropriate action in response.

When conducting conventional spectroscopic analyses, low detector signals for a characteristic of interest can sometimes be addressed by determining a derivative of the original spectrum. Obtaining the first derivative (slope) or second derivative (concavity) of the original spectrum may enhance small or subtle spectral features such that they can be more readily discerned. A key disadvantage associated with conventional derivative spectroscopy techniques is that spectral noise is also magnified when a derivative is determined, often making the derivative spectrum exceedingly noisy.

As an alternative to conventional spectroscopic techniques, optical computing devices containing an integrated computational element can be configured to specifically detect a characteristic of interest in a sample. Optical computing devices may utilize electromagnetic radiation to perform calculations, as opposed to the hardwired circuits of conventional electronic processors. Because optical computing devices can be specifically configured to detect a characteristic of interest, there may sometimes be a reduced need to conduct involved sample preparation steps prior to conducting an analysis. Further, optical computing devices are generally operationally simple and rugged. Thus, optical computing devices may be less impacted by the conditions that degrade the performance of conventional spectroscopic instruments, thereby making them well suited for field or process environments.

Unlike conventional spectroscopic analyses, which produce a spectrum that needs to undergo further interpretation to obtain a result, the ultimate output of an optical computing device is a real number that can be correlated with a characteristic of a sample. Correlation of the output of an optical computing device to a sample characteristic may be conducted, for example, by comparing the device's output for a sample against the device's output for one or more standards having a known value of a characteristic of interest. The output simplicity of optical computing devices is one of their more desirable features, which allows them to be deployed with little or no operator training.

SUMMARY OF THE INVENTION

The present disclosure relates to devices and methods for determining a characteristic of a sample using one or more integrated computational elements, and, more specifically, to devices and methods that computationally combine detector output signals produced from electromagnetic radiation that has optically interacted with one or more integrated computational elements.

In some embodiments, the present invention provides a device comprising: a first integrated computational element and a second integrated computational element, each integrated computational element having an optical function associated therewith, and the optical function of the second integrated computational element being at least partially offset in wavelength space relative to that of the first integrated computational element; an optional electromagnetic radiation source; at least one detector configured to receive electromagnetic radiation that has optically interacted with each integrated computational element and produce a first signal and a second signal associated therewith; and a signal processing unit operable for computationally combining the first signal and the second signal to determine a characteristic of a sample.

In some embodiments, the present invention provides a device comprising: an integrated computational element having an optical function associated therewith; an optional electromagnetic radiation source; a mechanism for altering an optical path length of electromagnetic radiation that optically interacts with the integrated computational element, such that the optical function associated with the integrated computational element is at least partially offset in wavelength space relative to itself when the electromagnetic radiation travels a first path length and a second path length while optically interacting with the integrated computational element; at least one detector configured to receive electromagnetic radiation that has optically interacted with the integrated computational element, thereby producing a first signal associated with the first path length and a second signal associated with the second path length; and a signal processing unit operable for computationally combining the first signal and the second signal to determine a characteristic of a sample.

In some embodiments, the present invention provides a method comprising: providing electromagnetic radiation that has optically interacted with or that has been emitted by a sample; optically interacting the electromagnetic radiation with a first integrated computational element and a second integrated computational element, each integrated computational element having an optical function associated therewith, the optical function of the second integrated computational element being at least partially offset in wavelength space relative to that of the first integrated computational element; detecting the electromagnetic radiation that has optically interacted with each integrated computational element, thereby producing a first signal and a second signal associated therewith; computationally combining the first signal and the second signal to produce a combined signal; and correlating the combined signal to a characteristic of the sample.

In some embodiments, the present invention provides a method comprising: providing electromagnetic radiation that has optically interacted with or that has been emitted by a sample; optically interacting the electromagnetic radiation with an integrated computational element such that the electromagnetic radiation optically interacts with a first path length, the integrated computational element having a first optical function associated with the first path length; altering the first path length to produce a second path length, the integrated computational element having a second optical function associated with the second path length that is at least partially offset in wavelength space relative to that associated with the first path length; detecting the electromagnetic radiation that has optically interacted with the integrated computational element at each path length, thereby producing a first signal and a second signal associated therewith; computationally combining the first signal and the second signal to produce a combined signal; and correlating the combined signal to a characteristic of the sample.

The features and advantages of the present invention will be readily apparent to one having ordinary skill in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to one having ordinary skill in the art and having the benefit of this disclosure.

DETAILED DESCRIPTION

The present disclosure relates to devices and methods for determining a characteristic of a sample using one or more integrated computational elements, and, more specifically, to devices and methods that computationally combine detector output signals produced from electromagnetic radiation that has optically interacted with one or more integrated computational elements.

Heretofore, it has been conventional practice in the field of optical computing devices to utilize one integrated computational element to detect one characteristic in a sample or multiple integrated computational elements to detect a like number of characteristics (i.e., in a one-to-one relationship). For example, commonly assigned U.S. Pat. No. 7,911,605 and United States Patent Application Publication 20100153048, each of which is incorporated herein by reference in its entirety, describe in great detail how to design and construct integrated computational elements having a desired performance for a single characteristic of interest. The theory behind optical computing and the operation of conventional optical computing devices is described in more detail in the following commonly owned United States patents and patent application Publications, each of which is incorporated herein by reference in its entirety: U.S. Pat. Nos. 6,198,531, 6,529,276, 7,123,844, 7,834,999, 7,911,605, 7,920,258, 2009/0219538, 2009/0219539, and 2009/0073433. Accordingly, the theory behind optical computing will not be discussed in any great detail herein unless needed to better describe one or more embodiments of the present disclosure. Although conventional optical computing devices containing multiple integrated computational elements have been heretofore described, the integrated computational elements of conventional optical computing devices are believed to have been configured to operate essentially independently of one another to analyze a single characteristic per integrated computational element. Applicant does not believe that there has been any recognition or suggestion in the art to computationally combine the output of two or more integrated computational elements to obtain a useful result.

As disclosed in commonly assigned U.S. patent applications Ser. Nos. 13/456,283, 13/456,350, 13/456,405, 13/456,302, 13/456,327, 13/456,379, and 13/456,443 each entitled "Methods and Devices For Optically Determining a Characteristic of a Substance," each filed concurrently herewith and incorporated herein by reference in its entirety, Applicant has discovered that the output of two or more integrated computational elements may be computationally combined to result in surprising improvements in detection performance for a single characteristic of interest. These benefits are significant and may be greater than additive in some cases. Furthermore, as disclosed in the co-pending applications, these benefits may be realized when the two or more integrated computational elements are associated with the characteristic of interest, disassociated with the characteristic of interest, or any combination thereof. It is particularly surprising that a disassociated integrated computational element may be beneficially utilized to determine a characteristic of interest, since it was heretofore believed that it was desirable for the integrated computational element to be associated with the characteristic of interest. In addition to the foregoing, combinations of integrated computational elements where at least one of the integrated computational elements demonstrates a positive response and at least one of the integrated computational elements demonstrates a negative response as the value of a characteristic increases may result in related surprising and beneficial improvements as well.

Although conventional optical computing can be an extremely powerful technique for analyzing a characteristic of a substance, the fact that it does not generate a spectrum, per se, has heretofore precluded the determination of derivative spectra via optical computing techniques. That is, since there is no spectrum generated in a conventional optical computing analysis, there has been no way to determine slope or concavity to better discern subtle spectral features. This general inability to determine derivative spectra by conventional optical computing techniques may be limiting for certain difficult-to-analyze characteristics (e.g., low abundance substances, two or more substances having similar spectral properties to one another, and the like).

In the present disclosure, we have further expanded upon the concept of computationally combining the output received from an integrated computational element to obtain a useful result. Specifically, we have conceptualized that if a detector output is received from electromagnetic radiation that has optically interacted with an integrated computational element and a like measurement is then made using an integrated computational element having a substantially similar optical function that is slightly offset in wavelength space from the original optical function, the computational combination of the detector outputs may result in an optical computing analogy to conventional derivative spectroscopy. In some of the present embodiments, two integrated computational elements may be specifically manufactured such that their optical functions, as defined herein, are offset slightly from one another in wavelength space and substantially similar over at least a portion of the wavelength space. Detector outputs obtained from each integrated computational element may be computationally combined according to the disclosure herein in order to determine a characteristic of a sample. As described above, techniques to fabricate an integrated computational element having a desired optical function are known to one having ordinary skill in the art. In some of the present embodiments, the optical function of an integrated computational element may be changed slightly between a first state and a second state, such that its optical function becomes slightly offset in wavelength space when in each state. Offset of the optical function may be accomplished by changing the angle of incidence of electromagnetic radiation on the integrated computational element, otherwise changing an optical path length of the optical interaction, and/or changing the index of refraction of at least one component of the integrated computational element. Thus, detecting electromagnetic radiation that has optically interacted with the integrated computational element in both states may allow a computational combination of the output to take place that achieves a like result to using separate integrated computation elements, as described above. Both approaches fall within the scope of computationally combining the output of an integrated computational element, even though only a single integrated computational element may be used in some embodiments.

In addition to potentially increasing the sensitivity of sample analyses using optical computing, the devices and methods described herein may present additional advantages over conventional derivative spectroscopic analyses. Specifically, the techniques described herein may not result in the noise enhancement that can occur in conventional derivative spectroscopic analyses. Further, the techniques described herein may allow substances that are spectroscopically similar to one another (i.e., have similar spectra) or otherwise not easily spectroscopically distinguishable to be better analyzed.

Optical computing devices employing an integrated computational element may be used to analyze various types of samples. One particular class of samples that may be analyzed by the devices and methods described herein are those that are commonly encountered in the oil and gas industry. Oil and gas samples, treatment fluids used in conjunction with the oil and gas industry, and produced fluids from a subterranean formation, for example, may be very complex and difficult to assay by conventional spectroscopic techniques, particularly without conducting detailed sample preparation. Uses of conventional optical computing devices in the analysis of fluids and other materials commonly encountered in the oil and gas industry are described in commonly owned U.S. patent application Ser. Nos. 13/198,915, 13/198,950, 13/198,972, 13/204,005, 13/204,046, 13/204,123, 13/204,165, 13/204,213, and 13/204,294, each filed on Aug. 5, 2011 and incorporated herein by reference in its entirety. In particular, the optical computing devices described herein may be used in any of the drilling phase, the stimulation phase, the production phase, and/or the remediation phase of subterranean operations. Illustrative materials that may be analyzed include, for example, treatment fluids (e.g., drilling fluids, acidizing fluids, fracturing fluids, and the like), pipeline fluids, bacteria, carrier fluids, source materials, produced water, produced hydrocarbon fluids, subterranean surfaces, and the like. Without limitation, the optical computing devices described herein may be used to assay, for example, composition and properties of a hydrocarbon fluid within or being produced from a subterranean formation (e.g., water content, gas-oil ratio, and the like), a treatment fluid within or being introduced to a subterranean formation, a spent or partially spent treatment fluid being produced from a subterranean formation, water being produced from a subterranean formation, a subterranean surface, and/or a pipeline surface. One of ordinary skill in the art will recognize that information regarding the composition and properties of these materials and others may provide valuable insight into the progress and outcome of a subterranean operation. Optical computing devices, including those described herein, provide a relatively low cost, rugged, and accurate system that can be used to analyze one or more characteristics of these type of samples and others. At a job site, the output of an optical computing device may be used to influence decision making in carrying out a job by determining a characteristic of a sample, thereby enabling real-time or near-real time process control. It will be appreciated, however, that the various devices disclosed herein may be used in other technology fields including, for example, the food and drug industry, industrial applications, mining industries, or any field where it may be advantageous to determine a characteristic of a sample in real-time or near real-time.

As used herein, the term "sample" and variations thereof refer to at least a portion of a substance of interest to be tested or otherwise evaluated using the optical computing devices described herein. The sample may possess a characteristic of interest. The sample may be any fluid or any solid substance or material such as, but not limited to, rock formations, concrete, and like solid surfaces.

As used herein, the term "fluid" refers to any substance that is capable of flowing, including particulate solids, liquids, gases, slurries, emulsions, powders, muds, glasses, any combination thereof, and the like. In some embodiments, the fluid can be an aqueous fluid, including water, mixtures of water and water-miscible fluids, and the like. In some embodiments, the fluid can be a non-aqueous fluid, including organic compounds (i.e., hydrocarbons, oil, a refined component of oil, petrochemical products, and the like). In some embodiments, the fluid can be a treatment fluid or a formation fluid. Illustrative gases that can be present in fluids include, for example, air, nitrogen, carbon dioxide, argon, helium, hydrogen sulfide, mercaptans, methane, ethane, propane, butane, other hydrocarbon gases, combinations thereof, and the like.

As used herein, the term "treatment fluid" refers to a fluid that is placed in a subterranean formation or in a pipeline in order to perform a desired function. Treatment fluids can be used in a variety of subterranean operations, including, but not limited to, drilling operations, production treatments, stimulation treatments, remedial treatments, fluid diversion operations, fracturing operations, secondary or tertiary enhanced oil recovery (EOR) operations, and the like. As used herein, the terms "treat," "treatment," "treating," and other grammatical equivalents thereof refer to any subterranean operation that uses a fluid in conjunction with performing a desired function and/or achieving a desired purpose. The terms "treat," "treatment," and "treating," as used herein, do not imply any particular action by the fluid or any particular component thereof unless otherwise specified. Treatment fluids for subterranean operations can include, for example, drilling fluids, fracturing fluids, acidizing fluids, conformance treatment fluids, damage control fluids, remediation fluids, scale removal and inhibition fluids, chemical floods, and the like.

As used herein, the term "characteristic" refers to a chemical, mechanical, or physical property of a substance. A characteristic of a substance may include a quantitative value of one or more chemical components therein. Such chemical components may be referred to as "analytes." Illustrative characteristics of a substance that can be monitored with the optical computing devices disclosed herein include, for example, chemical composition (identity and concentration, in total or of individual components), impurity content, pH, viscosity, density, ionic strength, total dissolved solids, total particulate solids, salt content, porosity, opacity, bacteria content, any combination thereof, and the like.

As used herein, the term "electromagnetic radiation" refers to radio waves, microwave radiation, infrared and near-infrared radiation, visible light, ultraviolet radiation, X-ray radiation, and gamma ray radiation.

As used herein, the term "optical computing device" refers to an optical device containing an integrated computational element that is configured to receive an input of electromagnetic radiation (e.g., from a substance or sample of the substance) and produce an output of electromagnetic radiation that is changed in some way so as to be readable by a detector, such that an output of the detector can be correlated with at least one characteristic of the substance. The output of electromagnetic radiation from the integrated computational element can be reflected electromagnetic radiation, transmitted electromagnetic radiation, and/or dispersed electromagnetic radiation. For each of these quantities, an integrated computational element will have a unique function associated therewith that is related to the amount of electromagnetic radiation that is reflected, transmitted, and/or dispersed. That is, there may be a function for reflected electromagnetic radiation, a function for transmitted electromagnetic radiation, and a function for dispersed electromagnetic radiation. As used herein, these functions will collectively be referred to as the "optical function" for a particular integrated computational element. It is to be recognized that reference to an optical function herein refers to any of these function types. Further discussion of optical functions follows below. As will be appreciated by one having ordinary skill in the art, whether reflected, dispersed, or transmitted electromagnetic radiation is analyzed by a detector will be dictated by numerous experimental factors that will be dependent on the chosen application (e.g., the type of sample and optical transparency of the sample being analyzed). In addition, emission and/or scattering of a sample (e.g., via fluorescence, luminescence, Raman scattering, and/or Raleigh scattering) can also be monitored by the optical computing devices.

As used herein, the term "optically interact" and variations thereof refer to the reflection, transmission, scattering, diffraction, or absorption of electromagnetic radiation by an integrated computational element or a sample. Accordingly, the term "optically interacted electromagnetic radiation" refers to electromagnetic radiation that has been reflected, transmitted, scattered, diffracted, or absorbed by, or emitted, or re-radiated from an integrated computational element or a sample.

The devices described herein may employ one or more integrated computational elements and receive two or more outputs therefrom in the course of determining a characteristic of interest in a sample. A brief description of an illustrative integrated computational element and the transmission/reflection function associated therewith follows below. Further details regarding integrated computational elements may be found, for example, in commonly owned U.S. Pat. No. 6,198,531, previously incorporated by reference in its entirety.

Figure 1:
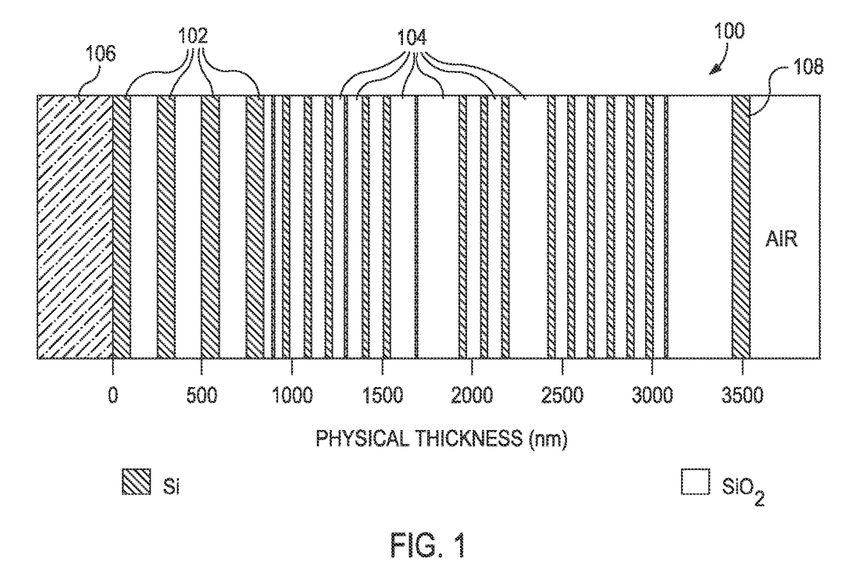
FIG. 1 shows a schematic of an illustrative integrated computational element (ICE).

FIG. 1 shows a schematic of an illustrative integrated computational element (ICE) 100. As illustrated in FIG. 1, ICE 100 may include a plurality of alternating layers 102 and 104, such as silicon (Si) and $SiO_2$ (quartz), respectively. In general, layers 102 and 104 contain materials whose indices of refraction are high and low, respectively. Other illustrative examples may include niobia and niobium, germanium and germania, MgF, and SiO. Additional materials having high and low indices of refraction can be envisioned by one having ordinary skill in the art, and the composition of layers 102 and 104 is not considered to be particularly limited. Layers 102 and 104 may be strategically deposited on optical substrate 106. In some embodiments, optical substrate 106 may be BK-7 optical glass. In other embodiments, optical substrate 106 may be formed from other types of optical materials such as, for example, quartz, sapphire, silicon, germanium, zinc selenide, zinc sulfide, various polymers (e.g., polycarbonates, polymethylmethacrylate, polyvinylchloride, and the like), diamond, ceramics, and the like. Opposite to optical substrate 106, ICE 100 may include layer 108 that is generally exposed to the environment of the device or installation in which it is used. The number and thickness of layers 102 and 104 may be determined based upon the spectral attributes of a sample characteristic acquired from via conventional spectroscopic analyses using a suitable spectroscopic instrument. For a given characteristic, a conventional spectrum may include one or more ranges of wavelengths that are uniquely influenced by that characteristic. It should be understood that illustrative ICE 100 of FIG. 1 has been presented for purposes of illustration only. Thus, it is not implied that ICE 100 is predictive for any particular characteristic of a given sample, nor do the number and thicknesses of layers 102 and 104 bear correlation to any particular characteristic of a given sample. Further, layers 102 and 104 are not necessarily drawn to scale and should therefore not be considered as limiting of the present disclosure. Moreover, one having ordinary skill in the art will readily recognize that the materials comprising layers 102 and 104 may vary depending on factors such as, for example, the application, cost of materials, and/or applicability of the material to the sample substance.

In some embodiments, the material within layers 102 and 104 can be doped, or two or more materials can be combined in a manner to achieve a desired optical response. In addition to solids, the ICE 100 may also contain liquids (e.g., water) and/or gases, optionally in combination with solids, in order to produce a desired optical response. In the case of gases and liquids, ICE 100 can contain a corresponding vessel (not shown) which houses the gases or liquids. Additional exemplary variations of ICE 100 may also include, for example, holographic optical elements, gratings, piezoelectric elements, light pipe, digital light pipe (DLP), and/or acousto-optic elements, for example, that can create transmission, reflection, scattering, and/or absorptive properties of interest.

The thicknesses and spacing of layers 102 and 104 may be determined using a variety of approximation methods based upon a conventional spectroscopic measurement of the characteristic of interest. These methods may include inverse Fourier transform (IFT) of the optical transmission spectrum and structuring ICE 100 as a physical representation of the IFT. The approximations convert the IFT into a structure based on known materials with constant refractive indices. Further information regarding the structures and design of exemplary integrated computational elements (also referred to as multivariate optical elements) is provided in *Applied Optics, Vol.* 35, pp. 5484-5492 (1996) and Vol. 29, pp. 2876-2893 (1990), which is incorporated by reference herein.

As previously discussed, layers 102 and 104 of ICE 100 exhibit different refractive indices. By properly selecting the materials of layers 102 and 104 and their relative spacing, ICE 100 may be configured to selectively transmit or reflect predetermined fractions of electromagnetic radiation at different wavelengths. A predetermined weighting coefficient or loading factor may be assigned to ICE 100 at each wavelength for transmission, reflection, or dispersion, thereby describing an optical function for each. The function of the relative weighting of transmitted electromagnetic radiation as a function of wavelength is referred to herein as a "transmission function." Correspondingly, the function of the relative weighting of reflected electromagnetic radiation as a function of wavelength is referred to herein as a "reflection function," and the function of relative weighting of dispersed electromagnetic radiation as a function of wavelength is referred to herein as a "dispersion function." For electromagnetic radiation that has been absorbed by the integrated computational element, the function of relative weighting is referred to as the "absorption function." As described previously, these functions will be collectively referred to herein as an "optical function" for a given integrated computational element. Unless otherwise noted, it should be recognized that any analysis described herein based upon a transmission function may be made in a like manner using a reflection function, an absorption function, or a dispersion function.

The weightings of the optical function may be referred to as a regression vector of the characteristic being analyzed. ICE 100 may be configured to calculate the dot product of the regression vector based upon the electromagnetic radiation input upon the ICE. As a result, the output electromagnetic radiation intensity of ICE 100, which is captured by a detector, is related to the characteristic of interest. Further details regarding how ICE 100 is able to distinguish and process electromagnetic radiation related to a characteristic of interest are described in, for example, commonly owned U.S. Pat. No. 6,198,531, previously incorporated herein by reference in its entirety.

Figure 2:
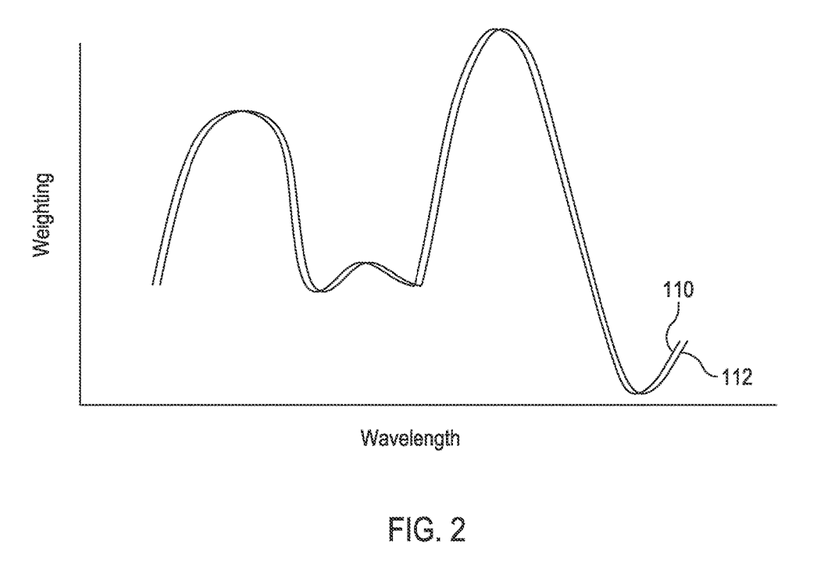
FIG. 2 shows a schematic of illustrative optical functions that replicate one another but are slightly offset in wavelength space.
Figure 3:
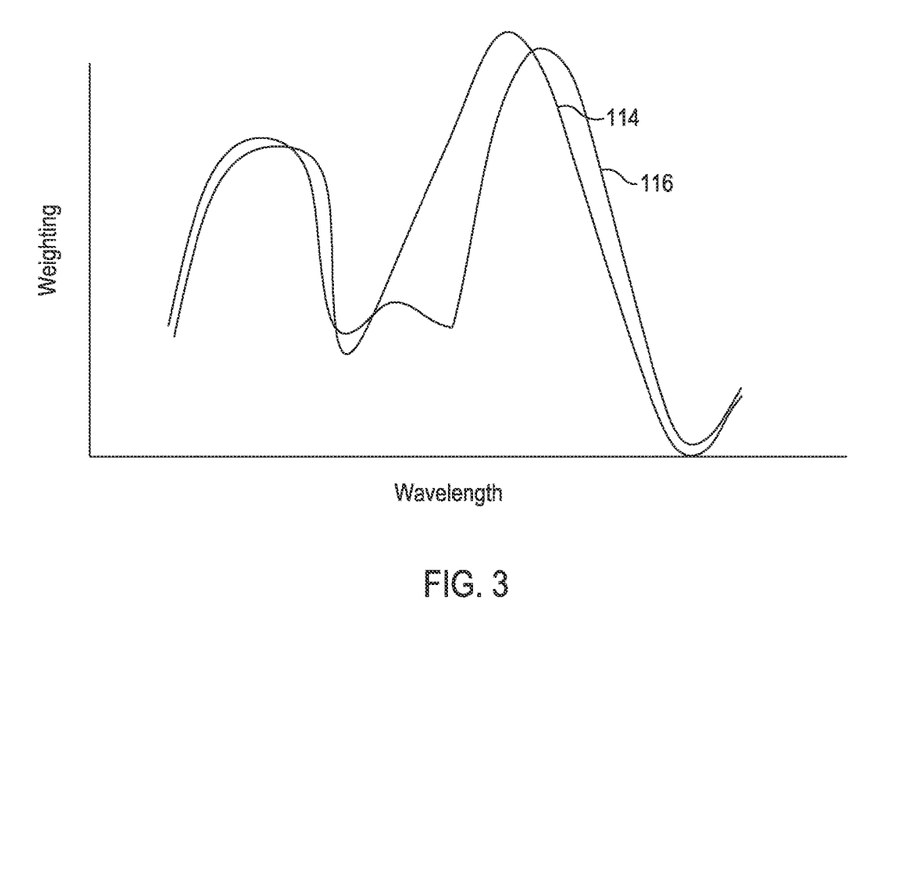
FIG. 3 shows a schematic of illustrative optical functions that are substantially similar, but not identical, in shape and are slightly offset in wavelength space.

As previously described, the devices and methods described herein may utilize output electromagnetic radiation from two integrated computational elements or a single integrated computational element in two different states having similar optical functions that are slightly offset from one another in wavelength space. FIG. 2 shows a schematic of illustrative optical functions 110 and 112 that replicate one another but are slightly offset in wavelength space. The amount of wavelength space offset is small relative to the wavelength itself. The transmission/reflection functions need not necessarily totally replicate one another, as shown in FIG. 2, but they may be substantially similar in shape over at least a portion of the wavelength space in other embodiments. FIG. 3 shows a schematic of illustrative optical functions 114 and 116 that are similar, but not identical, in shape and are offset in wavelength space. Again, it should be emphasized that the optical functions of FIGS. 2 and 3 have been presented for purposes of illustration only and should not be considered to be representative or predictive for a characteristic of any particular type of sample.

When two different integrated computational elements are used in the devices described herein, they may both be configured to be associated with the characteristic of interest, in some embodiments. As used herein, an integrated computational element that is associated with a characteristic is generally predictive of the characteristic when used alone. As described above, integrated computational elements have heretofore been specifically designed in their respective layers, thicknesses, and materials so as to correspond with the spectral attributes associated with the characteristic of interest. Although two or more integrated computational elements may be associated with a characteristic of interest, they may be designed differently from each other, if desired, thereby approximating or otherwise mimicking the regression vector of the characteristic of interest in entirely different ways.

In other embodiments, one of the integrated computational elements of the devices described herein can be associated with a characteristic of interest and one can be disassociated with a characteristic of interest, or both integrated computational elements can be disassociated with a characteristic of interest. As used herein, an integrated computational element that is disassociated with a characteristic is substantially non-predictive of the characteristic when used alone. Although one or both of the integrated computational elements may be disassociated with a characteristic of interest in the foregoing embodiments, once the outputs have been computationally combined according to the present embodiments, the combined result may be generally predictive for the characteristic.

As described above, in related embodiments, the optical function of a single integrated computational element may be altered slightly between a first state and a second state by altering its optical path length when optically interacting with electromagnetic radiation. For example, by altering the angle of incidence between the integrated computational element and incident electromagnetic radiation, the optical path length may be changed to result in a slight variance of the optical function in wavelength space. In other cases, a potential may be applied to an integrated computational element to change the refractive index of at least one component therein in order to accomplish a like result. Using a single integrated computational element that is switchable between two states in the present embodiments may be particularly advantageous, since it is anticipated that the optical function will closely mimic itself in the two states. This approach may avoid having to specifically fabricate two different integrated computational elements that have identical or substantially identical optical functions offset from one another in wavelength space. As one of ordinary skill in the art will recognize, as the two states become more divergent from one another, the differences in the optical functions will generally become greater.

Regardless of whether output is received from two different integrated computational elements or from a single integrated computational element in different states as a function of time, a detector output associated with electromagnetic radiation that has optically interacted with the integrated computational element(s) may be used to determine a characteristic of a sample. Since the optical functions of the two integrated computational elements or the single integrated computational element in two different states differ slightly from one another, they will produce a slightly different dot product (i.e., detector output) from one another when measuring a characteristic of interest. In some instances, the detector outputs alone may be individually correlatable with a characteristic of interest. However, according to the embodiments described herein, computationally combining the two detector outputs may allow more subtle differences to be discerned regarding a characteristic of interest. Computational combining the detector outputs can involve addition, subtraction, multiplication, division, or any combination thereof of the detector outputs. The computationally combined detector output of the sample may then be compared with the computationally combined detector output for one or more standards having a known value for a characteristic of interest.

In some embodiments, devices described herein can comprise a first integrated computational element and a second integrated computational element, each integrated computational element having an optical function associated therewith, and the optical function of the second integrated computational element being at least partially offset in wavelength space relative to that of the first integrated computational element; an optional electromagnetic radiation source; at least one detector configured to receive electromagnetic radiation that has optically interacted with each integrated computational element and produce a first signal and a second signal associated therewith; and a signal processing unit operable for computationally combining the first signal and the second signal to determine a characteristic of a sample.

In some embodiments, devices described herein can comprise: an integrated computational element having an optical function associated therewith; an optional electromagnetic radiation source; a mechanism for altering an optical path length of electromagnetic radiation that optically interacts with the integrated computational element, such that the optical function associated with the integrated computational element is at least partially offset in wavelength space relative to itself when the electromagnetic radiation travels a first path length and a second path length while optically interacting with the integrated computational element; at least one detector configured to receive electromagnetic radiation that has optically interacted with the integrated computational element, thereby producing a first signal associated with the first path length and a second signal associated with the second path length; and a signal processing unit operable for computationally combining the first signal and the second signal to determine a characteristic of a sample.

Various mechanisms may be used to alter the optical path length of electromagnetic radiation that optically interacts with the integrated computational element in embodiments in which a single integrated computational element is used. In some embodiments, the mechanism for altering the optical path length may be operable for changing an angle of incidence of electromagnetic radiation with the integrated computational element. In some embodiments, the mechanism may change an orientation of the integrated computational element relative to the electromagnetic radiation. In other embodiments, the mechanism may change an orientation of the electromagnetic radiation relative to the integrated computational element. In some embodiments, the mechanism may be operable for tilting the integrated computational element relative to electromagnetic radiation that is incident thereon. In some embodiments, the mechanism may comprise a reciprocating member that changes an orientation of the integrated computational element relative to electromagnetic radiation optically interacting therewith. Illustrative reciprocating members that may change an angle of incidence of electromagnetic radiation with an integrated computational element include, for example, a servo motor, a pendulum, a piston, a spring, an acoustoptic modulator, an electrooptic modulator, a diffraction grating, a holographic grating, a holographic optical element (HOE), a digital light pipe, any combination thereof, and the like. Thus, the present disclosure contemplates both moving the integrated computational element from a first orientation to a second orientation, and moving the electromagnetic radiation source to accomplish a like effect.

In some embodiments, the angle of incidence need not be altered to result in offset of the optical function. For example, in some embodiments, an index of refraction may be changed for at least one component of the integrated computational element to accomplish a like effect. In some embodiments, an electrical input may be applied to change an index of refraction of at least one component therein.

In some embodiments, the angle of incidence may be altered by forming the integrated computational element with a non-uniform thickness. In such embodiments, different portions of the integrated computational element may be optically interacted with electromagnetic radiation, and the optically interacted electromagnetic radiation that has optically interacted with each portion may be separately detected and quantified. Techniques for separating the electromagnetic radiation that has optically interacted with different portions of the integrated computational element will be familiar to one having ordinary skill in the art. It should be noted that this technique lies in stark contrast to the conventional use of integrated computational elements, where it has heretofore been desirable to maintain substantially uniform thicknesses to limit variability in determination of a characteristic.

The electromagnetic radiation interacting with the integrated computational element(s) of the devices described herein may come from any suitable source. In some embodiments, the electromagnetic radiation may come from an electromagnetic radiation source that is configured to impart electromagnetic radiation upon a sample and/or the integrated computational element(s). That is, in such embodiments, the source of electromagnetic radiation may be part of the device itself. In some or other embodiments, the electromagnetic radiation may be emitted by the sample or a material near the sample. This electromagnetic radiation may optically interact with the sample and/or the integrated computational element(s) to achieve a like result to that obtained using a separate electromagnetic radiation source. One of ordinary skill in the art will recognize various means through which a sample or other material may emit electromagnetic radiation. For example, through heating, a material may emit blackbody radiation that can optically interact with the integrated computational element(s) of the devices described herein. In other embodiments, a material may emit electromagnetic radiation by being radioactive or chemoluminescent, for example. In yet other embodiments, electromagnetic radiation may be emitted from a material in response to mechanical, magnetic, and/or electrical interaction with the material. For example, in some embodiments, an electrical potential may be placed across a sample in order to induce the production of electromagnetic radiation therefrom. Thus, an electromagnetic radiation source may be an optional feature in the devices described herein.

Various means are contemplated for computationally combining the first signal and the second signal obtained using the devices described herein. In various embodiments, the first signal and the second signal may be added to one another, subtracted from one another, multiplied by one another, divided by one another, or any combination thereof. That is, the signal processing unit of the devices described herein may determine the sum, difference, product, and/or quotient of the first signal and the second signal. For example, in some embodiments, the signal processing unit may determine a difference between the first signal and the second signal, the difference being correlatable to a characteristic of interest. The difference between the first signal and the second signal may be one result of the slight offset of the optical functions of the integrated computational element(s) and the difference in the corresponding dot products obtained therefrom.

As discussed above, a characteristic of a sample may be determined by computationally combining the detector outputs. In various embodiments, the computational combination may take place in a signal processing unit such as a computer, for example, which may be operating an algorithm suitable for performing the computational combination and determining a sample characteristic. In some embodiments, the algorithm may be configured to make predictions on how a bulk characteristic of the sample changes if the concentrations of one or more parameters are changed relative to one another. That is, in some embodiments, the algorithm may be configured to make predictions of an unmeasured characteristic based upon a value obtained for one or more directly measured characteristics. In some embodiments, the algorithm can produce an output that is readable by an operator who can manually take appropriate action, if needed, based upon the output. In some embodiments, the algorithm can take proactive control of a process in which the devices are used by automatically adjusting a characteristic in response to an out-of-range condition. The algorithm may include training that dictates how an out-of-range condition may most suitably be dealt with.

In some embodiments, the algorithm can be part of an artificial neural network configured to use the concentration of each detected analyte in order to evaluate the characteristic(s) of the sample and predict how to modify the sample to alter its properties in a desired way. Illustrative but non-limiting artificial neural networks suitable for use in the present embodiments are described in commonly owned United States Patent Application Publication 2009/0182693, which is incorporated herein by reference in its entirety. It is to be recognized that an artificial neural network can be trained using standards having known concentrations, compositions, and/or properties (e.g., characteristics), thereby generating a virtual library. As the virtual library available to the artificial neural network becomes larger, the network can become more capable of accurately predicting the characteristics of a sample.

It is to be recognized that the various embodiments herein relating to computer control and artificial neural networks, including various blocks, modules, elements, components, methods, algorithms, and the like can be implemented using computer hardware, software, combinations thereof, and the like. To illustrate this interchangeability of hardware and software, various illustrative blocks, modules, elements, components, methods, algorithms, and the like have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, algorithms, and the like described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory [e.g., random access memory (RAM), flash memory, read only memory (ROM), programmable read only memory (PROM), erasable read only memory (EPROM)], registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

In some embodiments, principal component analysis techniques may be used in the analysis by the signal processing unit. Such techniques can include partial least squares analysis, for example. The principal component analysis may be conducted using standard statistical analysis software packages including, for example, XL Stat for MICROSOFT® EXCEL®, the UNSCRAMBLER® from CAMO Software, and MATLAB® from MATH WORKS®).

In some embodiments, each integrated computational element in a device having two or more integrated computational elements may be associated with the characteristic being determined. In other embodiments, at least one of the integrated computational elements may be disassociated with the characteristic being determined. In some embodiments, the optical function of a second integrated computational element may be substantially similar in shape to that of a first integrated computational element over at least a portion of the wavelength space. That is, at least some portion of the optical functions are generally offset from one another. In some embodiments, both of the integrated computational elements may be disassociated from the characteristic of interest. As noted above, even when one or both of the integrated computational elements is disassociated from the characteristic of interest, their computational combination may be correlatable to the characteristic according to the embodiments described herein.

In some embodiments, the optical function of the second integrated computational element may be substantially identical in shape to that of the first integrated computational element and only offset in wavelength space. In other embodiments, the optical function of the second integrated computational element may be substantially similar in shape to that of the first integrated computational element over at least a portion of the wavelength space, while also being at least partially offset in wavelength space. As used herein, the term "substantially similar," as it relates to two optical functions, refers to two optical functions that are offset from one another in wavelength space that have at least a majority of shape similarity therebetween over at least a portion of their wavelength space. For example, two optical functions may be substantially similar over a relatively small wavelength range of the wavelength space. Techniques for comparing the degree of shape similarity between two functions will be familiar to one having ordinary skill in the art. In some embodiments, two transmission/reflection functions may be considered to be substantially similar when there is at least about 70% shape similarity therebetween. In some embodiments, two transmission/reflection functions may be considered to be substantially similar when there is at least about 80% shape similarity therebetween, or at least about 85% shape similarity therebetween, or at least about 90% shape similarity therebetween, or at least about 91% shape similarity therebetween, or at least about 92% shape similarity therebetween, or at least about 93% shape similarity therebetween, or at least about 94% shape similarity therebetween, or at least about 95% shape similarity therebetween, or at least about 96% shape similarity therebetween, or at least about 97% shape similarity therebetween, or at least about 98% shape similarity therebetween, or at least about 99% shape similarity therebetween, or at least about 99.5% shape similarity therebetween, or at least about 99.9% shape similarity therebetween. Again, shape similarity may refer to the entirety of the wavelength space or only a limited portion thereof.

The electromagnetic radiation that has optically interacted with the integrated computational element(s) may be received by one or more detectors. In some embodiments, a first detector may receive electromagnetic radiation that has optically interacted with the first integrated computational element, and a second detector may receive electromagnetic radiation that has optically interacted with the second integrated computational element. In other embodiments, electromagnetic radiation that has optically interacted with the first integrated computational element and electromagnetic radiation that has optically interacted with the second integrated computational element may be received by the same detector, but not at the same time. Detectors suitable for detecting various types of electromagnetic radiation will be familiar to one having ordinary skill in the art, any of which may be used in various embodiments described herein. Illustrative detectors that may be used in the various embodiments described herein include, for example, thermal detectors (e.g., thermopile or photoacoustic detectors), semiconductor detectors, piezoelectric detectors, charge-coupled device (CCD) detectors, video or array detectors, split detectors, photon detectors (e.g., photomultiplier tubes), photodiodes and photodiode arrays, any combination thereof, and the like. In addition, any other type of detector known to one having ordinary skill in the art may also be used.

Various configurations of the devices described herein are now set forth in some further detail. FIGS. 4-8 depict embodiments in which separate integrated computational elements are used. FIGS. 9A and 9B depict embodiments in which a single integrated computational element is used in a first orientation and a second orientation. Although the following FIGURES all depict an electromagnetic radiation source, it is to be recognized that the electromagnetic radiation that optically interacts with the integrated computational element(s) may be emitted by the sample or a material near the sample, as discussed above, and its use may therefore be optional. It is also to be recognized that the configurations depicted in the following FIGURES are meant to be illustrative in nature and should therefore be considered non-limiting. Various alternative configurations, modifications of the depicted configurations, and combinations thereof may be envisioned by one having ordinary skill in the art.

In the FIGURES that follow, electromagnetic radiation that has not optically interacted with an integrated computational element has been depicted with solid, single-headed arrows. Electromagnetic radiation that has optically interacted with an integrated computational element has been depicted with dashed, single-headed arrows. Signals produced from a detector and fed to a signal processing unit are depicted with dashed, double-headed arrows. Although not specifically shown in any of the following FIGURES, one or more spectral elements may be included in the devices in order to restrict the optical wavelengths and/or bandwidths of the system and thereby eliminate unwanted electromagnetic radiation existing in wavelength regions that have little or no importance. Such spectral elements can be located anywhere along the optical train, but are often employed immediately after the electromagnetic radiation source, if present. Illustrative spectral elements suitable for use in the devices described herein may be found in the commonly owned United States patents and patent application Publications previously incorporated by reference herein.

Figure 4:
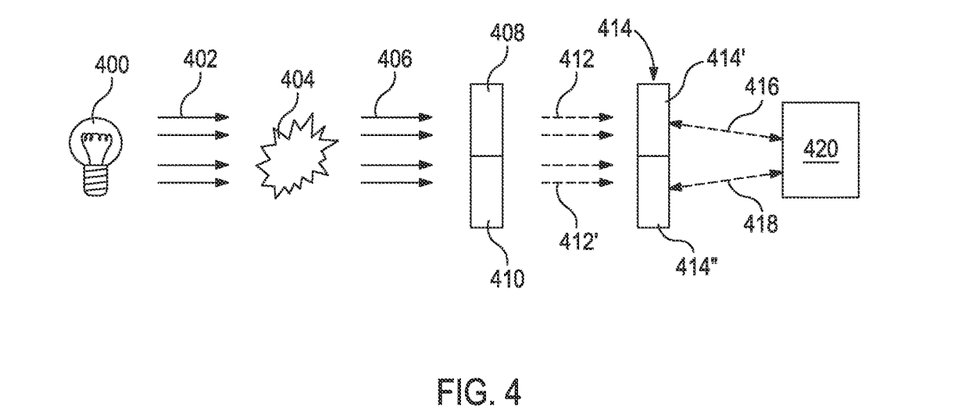
FIG. 4 shows a schematic of an illustrative optical computing device containing two integrated computational elements located adjacent to one another.

FIG. 4 shows a schematic of an illustrative optical computing device containing two integrated computational elements located adjacent to one another. As shown in FIG. 4, source 400 provides electromagnetic radiation 402, which is illuminated on sample 404. After optically interacting with sample 404, sample-interacted electromagnetic radiation 406, proceeds to integrated computational elements 408 and 410, where a portion of sample-interacted electromagnetic radiation 406 is optically interacted with each integrated computational element to produce optically interacted electromagnetic radiation 412 and 412'. Although FIG. 4 has depicted integrated computational elements 408 and 410 as being adjacent to one another and touching, other configurations in which integrated computational elements 408 and 410 are generally located parallel to one another are possible. For example, integrated computational elements 408 and 410 may be spaced apart from one another and/or offset with respect to electromagnetic radiation 412 and 412'. Further, in another alternative configuration, sample 404 may be placed after integrated computational elements 408 and 410, such that electromagnetic radiation 412 and 412' interacts with sample 404 before being detected.

Electromagnetic radiation 412 and 412' may be directed to detector 414, which contains detection elements 414' and 414" configured to receive electromagnetic radiation 412 and 412', respectively. Detection elements 414' and 414" produce first signal 416 and second signal 418, which are fed to signal processing unit 420 for correlation to a characteristic of interest. First signal 416 corresponds to electromagnetic radiation that has optically interacted with integrated computational element 408, and second signal 418 corresponds to electromagnetic radiation that has optically interacted with integrated computational element 410. In some embodiments, detector 414 may be configured to directly computationally combine first signal 416 and second signal 418. In other embodiments, computational combination may take place in signal processing unit 420 in order to determine a characteristic of sample 404. Thus, signal processing unit 420 need not necessarily comprise a separate entity, as drawn.

In an alternative configuration, detector 414 may be a single detector but configured to time multiplex the detection of electromagnetic radiation 412 and 412'. For example, integrated computational elements 408 and 410 may be configured to direct electromagnetic radiation 412 and 412' to detector 414 at distinct, non-overlapping time periods. Many ways are possible for accomplishing the foregoing including, for example, use of multiple sources of electromagnetic radiation, pulsing the source of electromagnetic radiation, mechanically positioning the integrated computational elements to interact with electromagnetic radiation at distinct times, deflection or diffraction of the electromagnetic radiation to interact with the integrated computational elements at distinct times, and any combination thereof.

Figure 5:
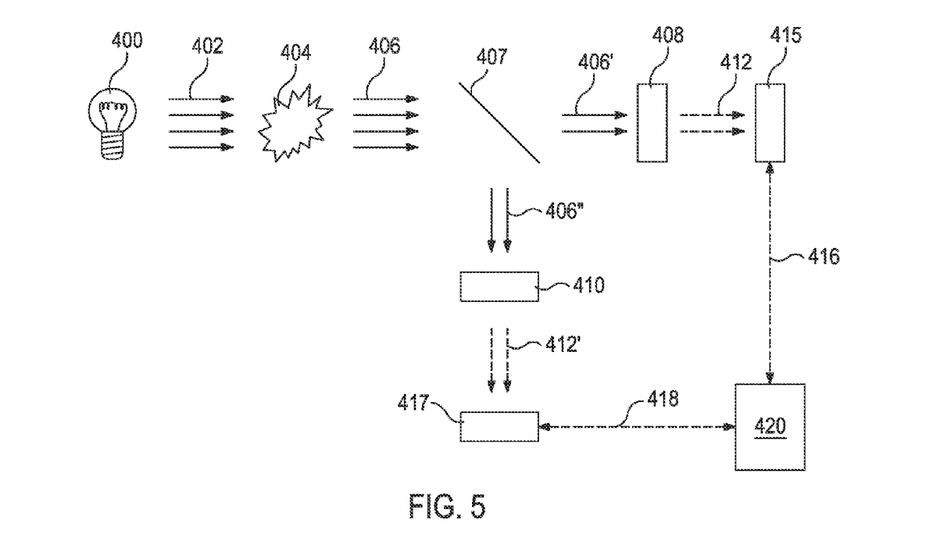
FIG. 5 shows a schematic of an illustrative optical computing device containing two integrated computational elements that are non-adjacent to one another.

FIG. 5 shows a schematic of an illustrative optical computing device containing two integrated computational elements that are non-adjacent to one another. Elements of FIG. 5 having similarity to those of FIG. 4 will be depicted with like reference characters and will not be described again in detail. As depicted in FIG. 5, sample-interacted electromagnetic radiation 406 impinges upon beam splitter 407, which directs electromagnetic radiation portion 406' to integrated computational element 408 and electromagnetic radiation portion 406" to integrated computational element 410. As in FIG. 4, optically interacted electromagnetic radiation 412 and 412' is produced from integrated computational elements 408 and 410, respectively. Optically interacted electromagnetic radiation 412 and 412' is then detected by detectors 415 and 417, respectively, to produce first signal 416 and second signal 418, which are then fed to signal processing unit 420 in order to determine a characteristic of sample 404. As before, signal processing unit 420 need not necessarily comprise a separate entity, as drawn.

Figure 6:
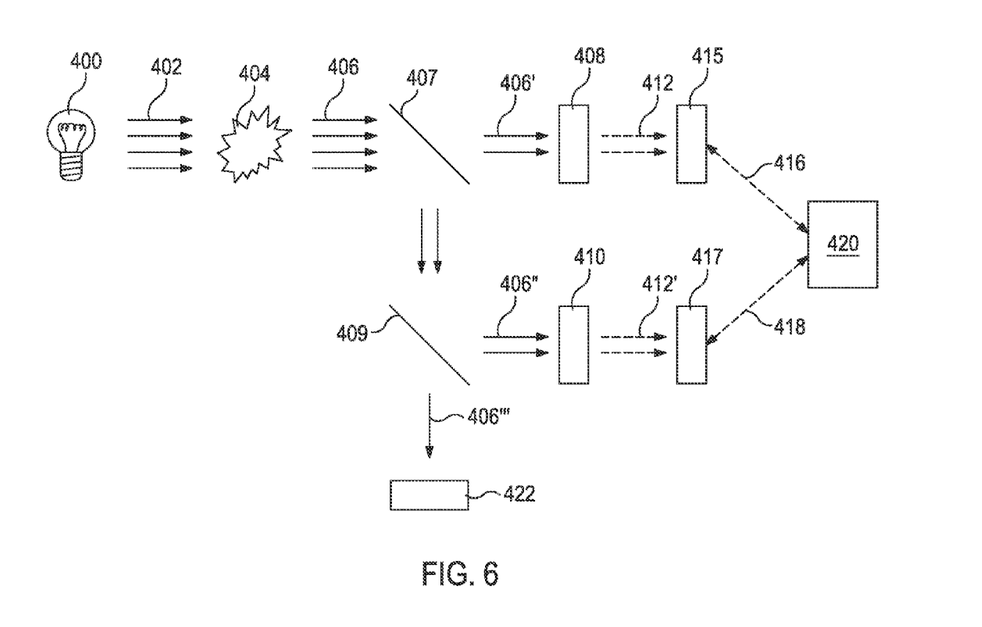
FIG. 6 shows a schematic of an illustrative optical computing device containing two integrated computational elements that are non-adjacent to one another, where multiple beam splitters have been used to direct the electromagnetic radiation.

FIG. 6 shows a schematic of an illustrative optical computing device containing two integrated computational elements that are non-adjacent to one another, where multiple beam splitters have been used to direct the electromagnetic radiation. Elements of FIG. 6 having similarity to those of FIGS. 4 and 5 will be depicted with like reference characters and will not not be described again in detail. As depicted in FIG. 6, sample-interacted electromagnetic radiation 406 is impinged upon beam splitter 407, which directs electromagnetic radiation portion 406' to integrated computational element 408. The remainder of sample-interacted electromagnetic radiation 406 is directed to beam splitter 409, which directs electromagnetic radiation portion 406" to integrated computational element 410. As before, optically interacted electromagnetic radiation 412 and 412' is produced from integrated computational elements 408 and 410, respectively. Optically interacted electromagnetic radiation 412 and 412' is then detected by detectors 415 and 417, respectively, to produce first signal 416 and second signal 418, which are then fed to signal processing unit 420 in order to determine a characteristic of sample 404. As before, signal processing unit 420 need not necessarily comprise a separate entity, as drawn.

Electromagnetic radiation portion 406''', which does not optically interact with an integrated computational element, may optionally be detected by detector 422. Detector 422 may be used to detect and correct for radiating deviations from source 400. In addition, detector 422 may help verify that source 400 is operating. Radiating deviations may arise from conditions such as, for example, output intensity fluctuations from the source, interferent fluctuations (e.g., dust or other interferents passing in front of the electromagnetic radiation source), coatings on windows included with the optical computing device, combinations thereof, and the like. In some embodiments, an output of detector 422 may be fed to signal processing unit 420 to be used in determining a characteristic of a sample.

Figure 7:
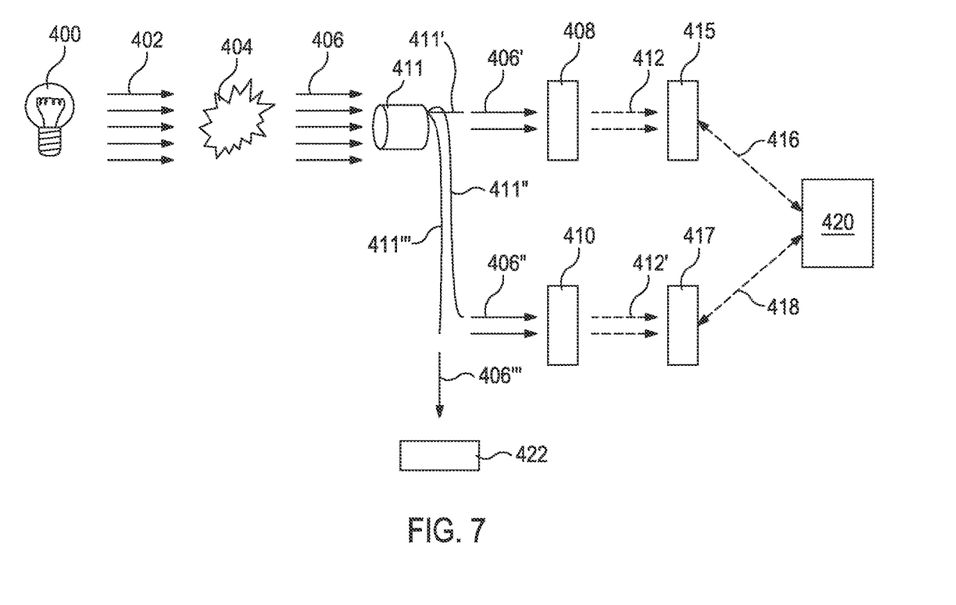
FIG. 7 shows a schematic of an illustrative optical computing device containing two integrated computational elements that are non-adjacent to one another, where an optical pipe has been used to direct the electromagnetic radiation.

FIG. 7 shows a schematic of an illustrative optical computing device containing two integrated computational elements that are non-adjacent to one another, where an optical pipe has been used to direct the electromagnetic radiation therein. In FIG. 7, beam splitters 407 and 409 of FIG. 6 have been replaced by optical pipe 411 containing a plurality of optical fibers therein. Optical fiber bundle 411' delivers electromagnetic radiation portion 406' to integrated computational element 408. Likewise, optical fiber bundle 411" delivers electromagnetic radiation portion 406" to integrated computational element 410. Optional optical fiber bundle 411''' can deliver electromagnetic radiation portion 406''' to optional detector 422, if present. The remaining elements of FIG. 7 are identical to those of FIG. 6 and will not be described again in further detail.

Figure 8:
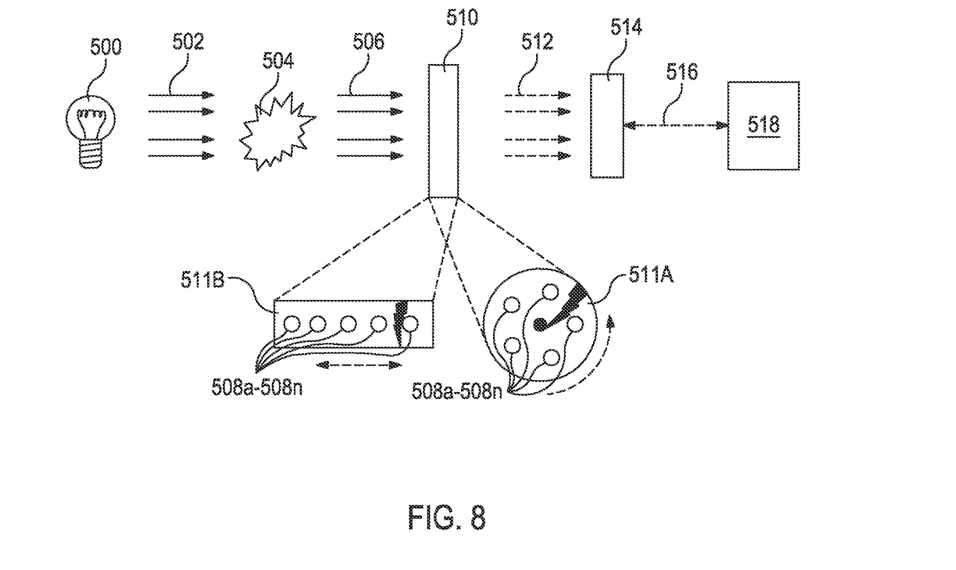
FIG. 8 shows a schematic of an illustrative optical computing device containing multiple integrated computational elements that are located on a movable assembly.
Figure 9A:
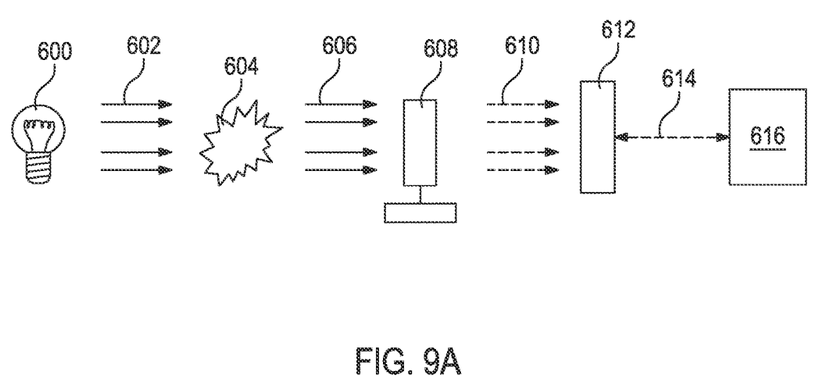
FIGS. 9A and 9B show a schematic of an illustrative optical computing device containing a single integrated computational element whose angle of incidence with electromagnetic radiation can be varied.
Figure 9B:
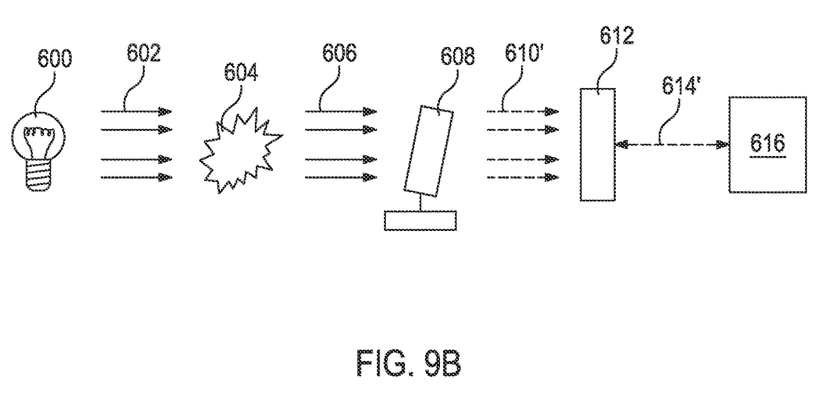

FIG. 8 shows a schematic of an illustrative optical computing device containing multiple integrated computational elements that are located on a movable assembly. As depicted in FIG. 8, source 500 provides electromagnetic radiation 502, which is illuminated on sample 504 to produce sample-interacted electromagnetic radiation 506. Sample-interacted electromagnetic radiation 506 interacts sequentially in time with integrated computational elements 508a-508n located on movable assembly 510. Movable assembly 510 is configured to rotate or translate integrated computational elements 508a-508n as a function of time, such that generally only one integrated computational element is producing optically interacted electromagnetic radiation 512 at any given time. Optically interacted electromagnetic radiation 512 is conveyed to detector 514, which produces signal 516 that is fed to signal processing unit 518. Since sample-interacted electromagnetic radiation 506 interacts with different integrated computational elements as a function of time, signal 516 resulting from optically interacted electromagnetic radiation 512 also varies as a function of time. Thus, time multiplexed signals 516 from detector 514 may be computationally combined by signal processing unit 518. As before, signal processing unit 518 need not necessarily comprise a separate entity, as drawn. It is to be recognized that any number of integrated computational elements greater than or equal to 2 may be present on movable assembly 510. In some embodiments, at least one of the integrated computational elements on movable assembly 510 may be used to correct for radiating deviations in source 500. In some embodiments, movable assembly 510 may be characterized as rotating disk 511A, having integrated computational elements 508a-508n radially disposed thereon. In other embodiments, movable assembly 510 may be characterized as linear array 5116, having integrated computational elements 508a-508n laterally offset from one another. During operation of the devices, movable assembly 510 may be cycled at any suitable rate. For example, when rotating disk 511A is used, the rotation rate may range between about 0.1 rpm to about 30,000 rpm in order to produce signal 516 that varies with time.

FIGS. 9A and 9B show a schematic of an illustrative optical computing device containing a single integrated computational element whose angle of incidence with electromagnetic radiation can be varied. FIG. 9A shows integrated computational element 608 in a first state, and FIG. 9B shows integrated computational element 608 tilted to a second state. As depicted in FIGS. 9A and 9B, source 600 provides electromagnetic radiation 602, which is illuminated on sample 604. After optically interacting with sample 604, sample-interacted electromagnetic radiation 606 impinges upon integrated computational element 608. In FIG. 9A, integrated computational element 608 is in a first state and produces optically interacted electromagnetic radiation 610. Optically interacted electromagnetic radiation 610 is delivered to detector 612, which produces signal 614. Signal 614 is then fed to signal processing unit 616. As before, signal processing unit 616 need not necessarily comprise a separate entity, as drawn.

After a period of time, integrated computational element 608 may be shifted to a second orientation, as generally depicted in FIG. 9B. In some embodiments, a reciprocating member may shift integrated computational element 608 from a first orientation to a second orientation. As discussed above, tilting integrated computational element 608 with respect to electromagnetic radiation incident thereon changes the optical path length, thereby resulting in the offsetting of the optical function. Although FIGS. 9A and 9B have been depicted using transmitted electromagnetic radiation, it is to be recognized that reflected or dispersed electromagnetic radiation can be used in alternative configurations of the devices. With continued reference to FIG. 9B, when in the second orientation, integrated computational element 608 produces optically interacted electromagnetic radiation 610', which is delivered to detector 612 to produce signal 614'. Signal 614' is then fed to signal processing unit 616 where it can be computationally combined with signal 614. As before, signal processing unit 616 need not necessarily comprise a separate entity, as drawn.

Although FIGS. 4-9B have generally shown electromagnetic radiation optically interacting with a sample before optically interacting with the integrated computational element(s), it is to be recognized that the embodiments depicted and described herein are not so limited in this manner. In any of the embodiments depicted and described herein, the sample may be located after the integrated computational element(s), such that optically interacted electromagnetic radiation illuminates the sample and is subsequently conveyed to one or more detectors.

Furthermore, although FIGS. 4-9B have generally depicted the optically interacted electromagnetic radiation produced by the integrated computational element(s) as being transmitted electromagnetic radiation, it is to be recognized that the reflected, diffusely reflected, or dispersed electromagnetic radiation may be detected and analyzed in a like manner using devices that are so configured. Likewise, electromagnetic radiation may be reflected from the sample, instead of being transmitted therethrough, as depicted.

In some embodiments, methods for analyzing a characteristic of a sample are described herein. In some embodiments, the methods can comprise detecting electromagnetic radiation that has optically interacted with two integrated computational elements, where the integrated computational elements have optical functions that are at least partially offset in wavelength space from one another. In such embodiments, the electromagnetic radiation may optically interact with both integrated computational elements at the same time, or with a first integrated computational element at a first time and a second integrated computational element at a second time. In other embodiments, the methods can comprise detecting electromagnetic radiation that has optically interacted with a single integrated computational element at different points in time, where a path length of the optical interaction with the integrated computational element has been altered so as to change the optical function of the integrated computational element at various points in time.

In some embodiments, the methods can comprise: providing electromagnetic radiation that has optically interacted with or that has been emitted by a sample; optically interacting the electromagnetic radiation with a first integrated computational element and a second integrated computational element, each integrated computational element having an optical function associated therewith, the optical function of the second integrated computational element being at least partially offset in wavelength space relative to that of the first integrated computational element; detecting the electromagnetic radiation that has optically interacted with each integrated computational element, thereby producing a first signal and a second signal associated therewith; computationally combining the first signal and the second signal to produce a combined signal; and correlating the combined signal to a characteristic of the sample.

In other embodiments, the methods can comprise: providing electromagnetic radiation that has optically interacted with or that has been emitted by a sample; optically interacting the electromagnetic radiation with an integrated computational element such that the electromagnetic radiation optically interacts with a first path length, the integrated computational element having a first optical function associated with the first path length; altering the first path length to produce a second path length, the integrated computational element having a second optical function associated with the second path length that is at least partially offset in wavelength space relative to that associated with the first path length; detecting the electromagnetic radiation that has optically interacted with the integrated computational element at each path length, thereby producing a first signal and a second signal associated therewith; computationally combining the first signal and the second signal to produce a combined signal; and correlating the combined signal to a characteristic of the sample.

In some embodiments, altering the first path length to produce a second path length may comprise changing an orientation of the integrated computational element relative to electromagnetic radiation optically interacting therewith, such that an angle of incidence is changed.

In some embodiments, altering the first path length to produce a second path length may comprise changing an orientation of the electromagnetic radiation relative to the integrated computational element, such that an angle of incidence is changed.

In some embodiments, altering the first path length to produce a second path length may comprise applying an electrical input to the integrated computational element that changes an index of refraction of at least one component therein.

In some embodiments, altering the first path length to produce a second path length may comprise forming the integrated computational element such that it has a non-uniform thickness. In some embodiments, the methods may further comprise directing electromagnetic radiation to different regions of the integrated computational element having a non-uniform thickness, such that a first portion of the electromagnetic radiation experiences a first path length during optical interaction and a second portion of the electromagnetic radiation experiences a second path length during optical interaction.

In some embodiments, computationally combining the first signal and the second signal can comprise determining the sum of the first signal and the second signal to produce a combined signal. In some embodiments, computationally combining the first signal and the second signal can comprise determining a difference between the first signal and the second signal to produce a combined signal. In some embodiments, computationally combining the first signal and the second signal can comprise determining the product of the first signal and the second signal to produce a combined signal. In some embodiments, computationally combining the first signal and the second signal can comprise determining the quotient of the first signal and the second signal, or vice versa, to produce a combined signal. In some embodiments, one or both of the signals may be multiplied or divided by a weighting constant, if desired, when performing the computational combination. Principal component analysis may also be performed in some embodiments.

In various embodiments, correlating the combined signal to a characteristic of the sample can comprise comparing the combined signal of the sample to a combined signal of at least one standard having a known value of the characteristic. For example, in some embodiments, one or more standards having a known value for a characteristic may be measured using the devices described herein. That is, the computational combination of the first signal and the second signal for the calibration standard(s) may be directly compared to the computational combination of the first signal and the second signal for the sample in order to determine a value of the sample characteristic. Such comparison techniques will be familiar to one having ordinary skill in the art and can include, for example, techniques such as calibration curve determination, and the like.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A device comprising:
   a first integrated computational element and a second integrated computational element disposed on a rotating disk, each integrated computational element having an optical function associated therewith, and the optical function of the second integrated computational element being at least partially offset in wavelength space relative to that of the first integrated computational element;
   wherein the optical function of the first integrated computational element and the optical function of the second integrated computational element differ from one another and encompass at least some of the same wavelengths within the wavelength space; and
   wherein the first integrated computational element and the second integrated computational element analyze for a single characteristic of a sample;
   an optional electromagnetic radiation source;
   at least one detector configured to receive electromagnetic radiation that has optically interacted with each integrated computational element and produce a first signal and a second signal associated therewith; and
   a signal processing unit operable for computationally combining the first signal and the second signal to determine the single characteristic.

2. The device of claim 1, wherein the signal processing unit determines a difference between the first signal and the second signal.

3. The device of claim 1, wherein each integrated computational element is associated with the single characteristic being determined.

4. The device of claim 1, wherein at least one of the integrated computational elements is disassociated with the single characteristic being determined.

5. The device of claim 1, wherein the optical function of the second integrated computational element is substantially similar in shape to that of the first integrated computational element over at least a portion of the wavelength space.

6. The device of claim 1, wherein a first detector receives the electromagnetic radiation that has optically interacted with the first integrated computational element and a second detector receives the electromagnetic radiation that has optically interacted with the second integrated computational element.

7. The device of claim 1, wherein the electromagnetic radiation that has optically interacted with the first integrated computational element and the electromagnetic radiation that has optically interacted with the second integrated computational element are received by the same detector, but not at the same time.

8. The device of claim 1, wherein the optical function of the first integrated computational element and the optical function of the second integrated computational element have at least a majority of shape similarity over the wavelength space.

9. The device of claim 8, wherein the optical function of the first integrated computational element and the optical function of the second integrated computational element have at least about 70% shape similarity over the wavelength space.

10. A method comprising:
    providing electromagnetic radiation that has optically interacted with or that has been emitted by a sample;
    optically interacting the electromagnetic radiation with a first integrated computational element and a second integrated computational element that are disposed on a rotating disk, each integrated computational element having an optical function associated therewith, the optical function of the second integrated computational element being at least partially offset in wavelength space relative to that of the first integrated computational element;
    wherein the optical function of the first integrated computational element and the optical function of the second integrated computational element differ from one another and encompass at least some of the same wavelengths within the wavelength space; and
    wherein the first integrated computational element and the second integrated computational element analyze for a single characteristic of the sample;
    detecting the electromagnetic radiation that has optically interacted with each integrated computational element, thereby producing a first signal and a second signal associated therewith;
    computationally combining the first signal and the second signal to produce a combined signal; and
    correlating the combined signal to the single characteristic of the sample.

11. The method of claim 10, wherein the optical function of the second integrated computational element is substantially similar in shape to that of the first integrated computational element over at least a portion of the wavelength space.

12. The method of claim 10, wherein each integrated computational element is associated with the single characteristic being determined.

13. The method of claim 10, wherein at least one of the integrated computational elements is disassociated with the single characteristic being determined.

14. The method of claim 10, wherein correlating the combined signal comprises comparing the combined signal of the sample to a combined signal of at least one standard having a known value of the single characteristic.

15. The method of claim 10, wherein the optical function of the first integrated computational element and the optical function of the second integrated computational element have at least a majority of shape similarity over the wavelength space.

16. The method of claim 15, wherein the optical function of the first integrated computational element and the optical function of the second integrated computational element have at least about 70% shape similarity over the wavelength space.

* * * * *